United States Patent
Tsai et al.

(10) Patent No.: US 11,628,005 B2
(45) Date of Patent: Apr. 18, 2023

(54) TOOL FOR BONE IMPLANT

(71) Applicant: METAL INDUSTRIES RESEARCH & DEVELOPMENT CENTRE, Kaohsiung (TW)

(72) Inventors: Tung-Lin Tsai, Tainan (TW); Chun-Chieh Tseng, Kaohsiung (TW); Chun-Ming Chen, Kaohsiung (TW); Yue-Jun Wang, New Taipei (TW); Hsin-Fei Wang, Pingtung County (TW); Pei-Hua Wang, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 238 days.

(21) Appl. No.: 17/110,759

(22) Filed: Dec. 3, 2020

(65) Prior Publication Data
US 2022/0175437 A1 Jun. 9, 2022

(51) Int. Cl.
*A61B 17/88* (2006.01)
*A61B 90/00* (2016.01)
*A61B 17/00* (2006.01)

(52) U.S. Cl.
CPC ...... *A61B 17/8883* (2013.01); *A61B 17/8891* (2013.01); *A61B 90/06* (2016.02); *A61B 90/08* (2016.02); *A61B 2017/00477* (2013.01); *A61B 2090/066* (2016.02); *A61B 2090/0807* (2016.02)

(58) Field of Classification Search
CPC ........... A61B 17/8875–17/8891; B25B 13/462
See application file for complete search history.

(56) References Cited

U.S. PATENT DOCUMENTS

| | | | | |
|---|---|---|---|---|
| 6,109,150 | A * | 8/2000 | Saccomanno, III | A61C 8/0089 81/479 |
| 7,597,032 | B2 * | 10/2009 | Baumgartner | A61C 8/0089 81/60 |
| 11,173,582 | B2 * | 11/2021 | Ruetschi | B25B 13/462 |
| 2006/0155297 | A1 * | 7/2006 | Ainsworth | A61B 17/7055 606/99 |
| 2008/0070190 | A1 * | 3/2008 | Baumgartner | A61B 17/8891 433/141 |
| 2013/0340574 | A1 * | 12/2013 | Buchanan | B25B 13/465 81/60 |
| 2020/0323612 | A1 | 10/2020 | Kim | |

FOREIGN PATENT DOCUMENTS

JP S48106589 U 12/1973
JP 2019136315 A 8/2019

* cited by examiner

*Primary Examiner* — Zade Coley
(74) *Attorney, Agent, or Firm* — Alan D. Kamrath; Karin L. Williams; Mayer & Williams PC

(57) ABSTRACT

A tool for a bone implant includes a rod and an adaptor. The rod includes a coupling portion having a through-hole. The rod further includes a measuring arm connected to the coupling portion and a force applying arm connected to the coupling portion. The measuring arm includes a first extension section having a first indicator portion, and the force applying arm includes a second extension section having a second indicator portion. The force applying arm is elastically deformable away from the measuring arm to displace the second extension section relative to the first extension section. The adaptor is coupled in the through-hole and includes an outer ring and an inner ring. The outer ring is rotatable relative to the inner ring in a single direction.

9 Claims, 7 Drawing Sheets

TOOL FOR BONE IMPLANT

BACKGROUND OF THE INVENTION

1. Field of the Invention

The present invention relates to a tool for operation and, more particularly, to a tool for a bone implant for proceeding with implantation of a bone nail.

2. Description of the Related Art

In a treatment of a bone injured due to external force, diseases, or degeneration, a bone nail can be implanted into the injured bone to increase the structural strength of the bone or to fix the bone for healing. Generally, during the implantation of the bone nail, a manual operative tool similar to a screwdriver is used to screw the bone nail into the bone. After the bone nail is screwed into the bone, a stress squeezing the bone tissue is incurred. According to domestic and foreign researches on bone injury, osteonecrosis occurs due to excessive stress, but proper stress can increase the growing speeding of the bone tissue. Thus, during the implantation of the bone nail, the stress squeezing the bone tissue is controlled by the torque rotating the bone nail. However, conventional instruments for measuring the torque are precision instruments that cannot proceed with disinfection and sterilization and are, thus, not suitable for use in the implantation of the bone nail. Currently available operative tools cannot allow an operator to know the torque every time he or she controls the rotation, such that the operator might easily apply an excessive force that adversely affects the bone tissue.

In view of the above, improvement to the conventional tools is desired.

SUMMARY OF THE INVENTION

To solve the above problems, it is an objective of the present invention to provide a tool for a bone implant, which tool can show the torque while rotating a bone nail.

It is another objective of the present invention to provide a tool for a bone implant, which can proceed with disinfection and sterilization at a high temperature.

As used herein, the term "a" or "an" for describing the number of the elements and members of the present invention is used for convenience, provides the general meaning of the scope of the present invention, and should be interpreted to include one or at least one. Furthermore, unless explicitly indicated otherwise, the concept of a single component also includes the case of plural components.

As used herein, the term "coupling", "engagement", "assembly", or similar terms is used to include separation of connected members without destroying the members after connection or inseparable connection of the members after connection. A person having ordinary skill in the art would be able to select according to desired demands in the material or assembly of the members to be connected.

A tool for a bone implant according to the present invention comprises a rod and an adaptor. The rod includes a coupling portion having a through-hole. The rod further includes a measuring arm connected to the coupling portion and a force applying arm connected to the coupling portion. The measuring arm includes a first extension section having a first indicator portion. The force applying arm includes a second extension section having a second indicator portion. The force applying arm is elastically deformable away from the measuring arm to displace the second extension section relative to the first extension section. The adaptor includes an outer ring and an inner ring. Each of two open ends at upper and lower sides of the outer ring has an annular ledge. The inner ring is elastically deformable relative to the outer ring to permit the inner ring to be disposed between the annular ledges. The outer ring is coupled in the through-hole of the rod. The outer ring includes an outer periphery having a plurality of first toothed structures. An inner periphery of the through-hole of the rod does not match with the plurality of first toothed structures to reduce a contact area between the outer periphery of the outer ring and the inner periphery of the through-hole. The inner ring includes an inner periphery having a plurality of second toothed structures. The outer ring is rotatable relative to the inner ring in a single direction.

Thus, according to the tool for a bone implant according to the present invention, the rod can be rotated by applying a force to the force applying arm. The torque created by the force applying arm can displace the second extension section relative to the first extension section, and the torque magnitude created by the force applying arm can be learned from the position of the second indicator portion relative to the first indicator portion. Thus, when the user screws the bone nail unit into a predetermined portion, the magnitude of the created torque can be known, and the torque can be controlled not to exceed 35 Ncm, avoiding injury to the bone tissue by an excessive torque while permitting the rod to be rotated by a most proper torque. Furthermore, the tool for a bone implant according to the present invention measures the torque magnitude with the elastic deformation of the force applying arm of the rod, and the rod can be disinfected and sterilized at high temperature, which is suitable for bone nail implantation, reducing the operation risks and improving the quality of the medical treatment.

In an example, the rod is made of a titanium alloy. Thus, the rod is flexible and has certain rigidity, increasing the use convenience.

In an example, the titanium alloy is $Ti_6Al_4V$. Thus, the rod is flexible and has certain rigidity, increasing the use convenience.

In an example, the coupling portion includes an expansion gap having an open end intercommunicating with the through-hole. The expansion gap extends in the coupling portion to form a closed end. Thus, the diameter of the through-hole can be slightly increased to receive an adaptor of a larger diameter, increasing the coupling stability between the through-hole and the adaptor.

In an example, the expansion gap extends in the coupling portion along a circular path. Thus, the extension length of the expansion gap is increased to uniformly distribute the stress resulting from diametrical expansion of the through-hole.

In an example, the measuring arm and the force applying arm are disconnected from each other, and the measuring arm and the force applying arm are juxtaposed and connected to the coupling portion. By using the junction between the force applying arm and the coupling portion as a fulcrum, the force applying arm can elastically deform away from the measuring arm, such that the torque applied to the force applying arm can be measured.

In an example, the measuring arm includes a housing having an opening, and the second extension extends into the housing via the opening. Thus, the second extension section can be located in the housing and displaceable relative to the first extension section, such that the torque applied to the force applying arm can be measured.

In an example, the minimum cross sectional area of a junction between the force applying arm and the coupling portion is smaller than 50% of the minimum cross sectional area of the coupling portion. Thus, the force applying arm can easily deform elastically about the fulcrum, increasing the use convenience.

In an example, at least one of an outer periphery of the outer ring and an inner periphery of the inner ring is toothed. Thus, the contact area between the outer ring and the inner periphery of the through-hole or the contact area between the inner ring and the bone nail unit can be reduced, allowing easy installation and detachment of the adaptor and the bone nail unit.

In an example, the outer ring includes an inner periphery having at least one unidirectional tooth. The inner ring includes an outer periphery having a plurality of ratchet teeth. The outer ring is capable of driving the inner ring to rotate in the single direction only. Thus, the user can rotate the rod in the clockwise direction and the counterclockwise direction in an alternating fashion to screw the bone nail unit into the bone tissue. As a result, the user can still proceed with the operation in a portion permitting limited rotation, increasing the use convenience.

The present invention will become clearer in light of the following detailed description of illustrative embodiments of this invention described in connection with the drawings.

Figure 1:
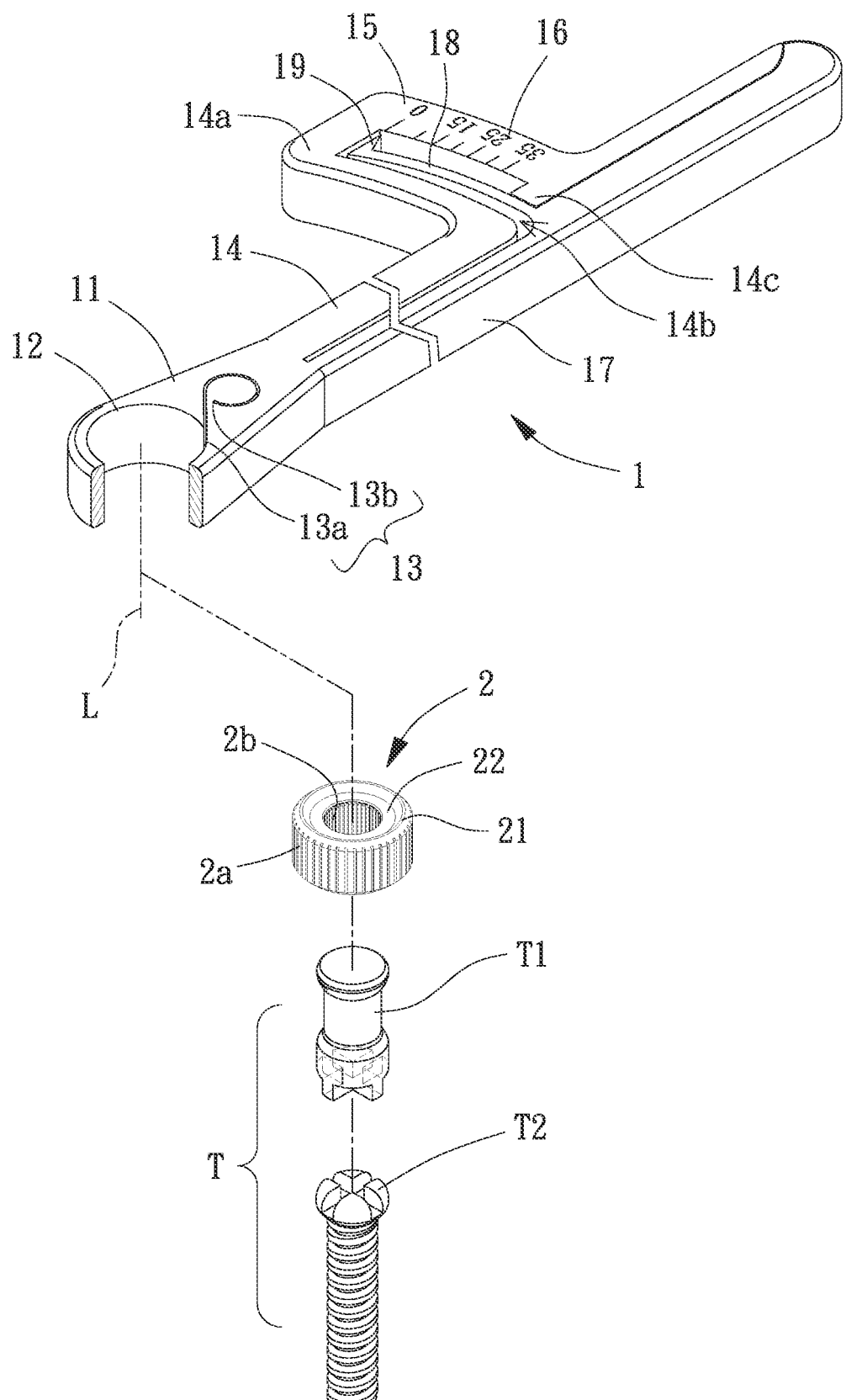
FIG. 1 is an exploded, perspective view of a tool for a bone implant of an embodiment according to the present invention.

When the terms "front", "rear", "left", "right", "up", "down", "top", "bottom", "inner", "outer", "side", and similar terms are used herein, it should be understood that these terms have reference only to the structure shown in the drawings as it would appear to a person viewing the drawings and are utilized only to facilitate describing the invention, rather than restricting the invention.

DETAILED DESCRIPTION OF THE INVENTION

Figure 2:
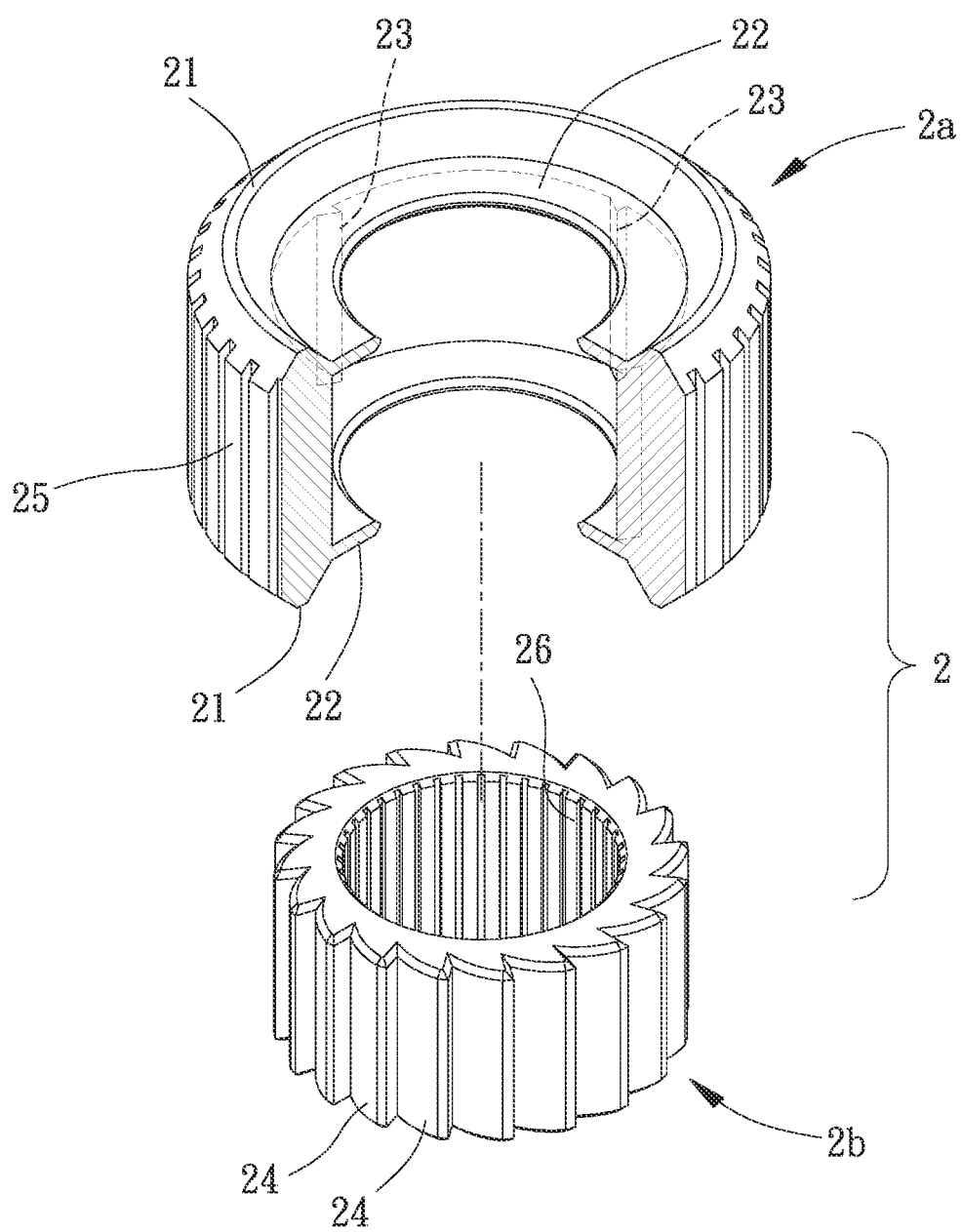
FIG. 2 is an exploded, perspective view of an adaptor of the tool of FIG. 1.

With reference to FIGS. 1 and 2, a tool for a bone implant of an embodiment according to the present invention includes a rod 1 and an adaptor 2 coupled to the rod 1. The adaptor 2 can be used to couple with a conventional bone nail unit T.

The rod 1 is made of material with flexibility and certain rigidity, such that the rod 1 has sufficient strength for force application by a user. For example, the rod 1 can be made of stainless steel and preferably a titanium alloy. In this embodiment, the rod is made of $Ti_6Al_4V$. The rod 1 includes a coupling portion 11 having a through-hole 12. The through-hole 12 can receive the adaptor 2. The through-hole 12 has a longitudinal axis L passing through its geometric center. The rod 1 can rotate about the longitudinal axis L. The coupling portion 11 is preferably located on an end of the rod 1. Thus, the user can apply a force by another end of the rod 1 with a longer arm of force, providing a labor saving effect. In this embodiment, the coupling portion 11 includes an expansion gap 13 extending through two opposite faces of the coupling portion 11. The expansion gap 13 includes an open end 13a intercommunicating with the through-hole 12. Furthermore, the expansion gap 13 extends in the coupling portion 11 to form a closed end 13b. Thus, the expansion gap 13 forms an elastically deformable space permitting slight expansion of the diameter of the expansion gap 13, such that the through-hole 12 can receive an adaptor 2 of a larger diameter, increasing the coupling stability between the through-hole 12 and the adaptor 2. Furthermore, the expansion gap 13 preferably extends in the coupling portion 11 along a circular path, increasing the extension length of the expansion gap 13. Thus, the stress resulting from diametrical expansion of the through-hole 12 can be distributed uniformly.

Figure 3:
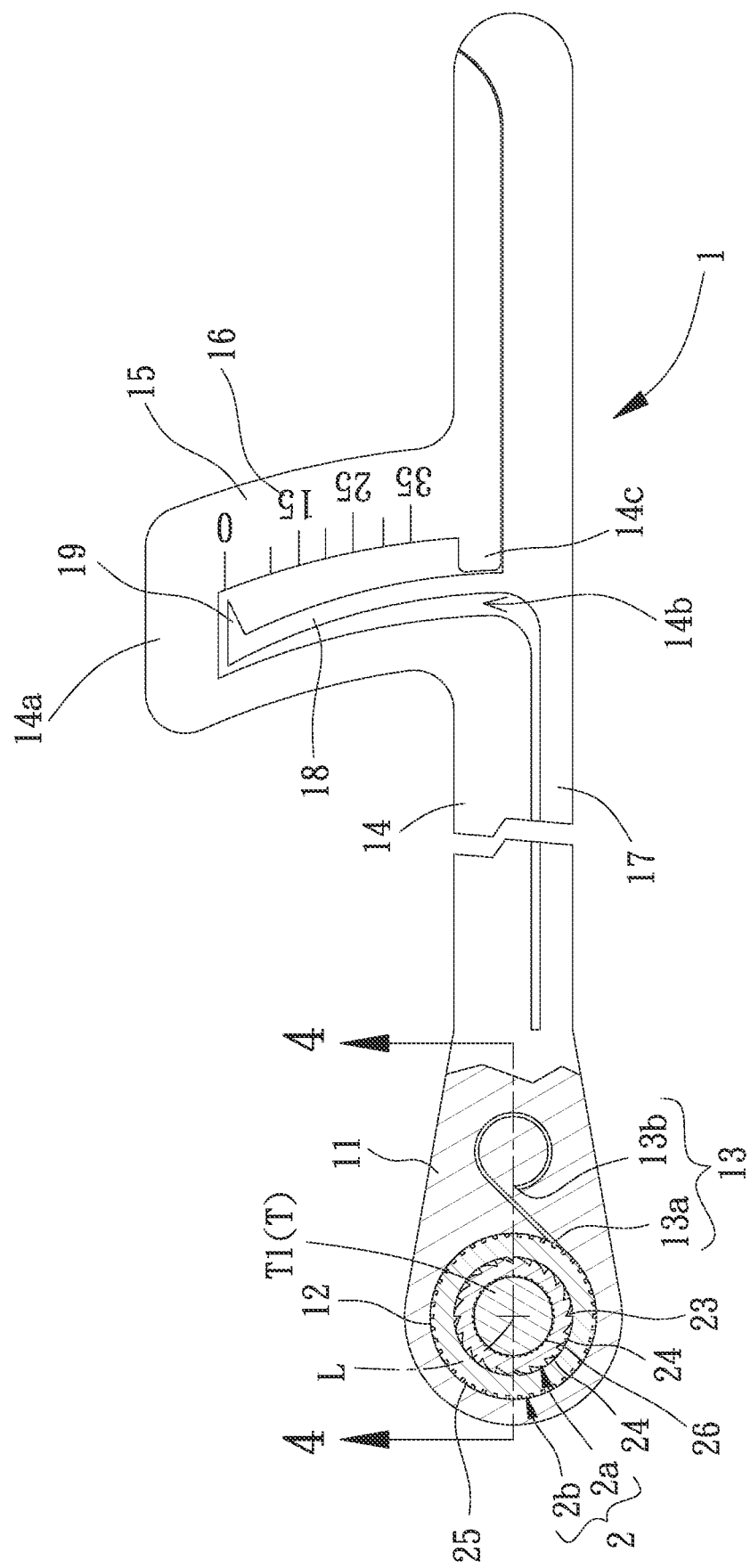
FIG. 3 is a partially sectioned view of the tool of FIG. 1 after assembly.

With reference to FIGS. 1 and 3, the rod 1 further includes a measuring arm 14. Preferably, an end of the measuring arm 14 is connected to the coupling portion 11 by integral formation. The measuring arm 14 includes a first extension section 15 extending beyond a side of the measuring arm 14. A virtual circumferential direction D is formed when the rod 1 rotates about the longitudinal axis L. The first extension section 15 can extend in the circumferential direction D. In this embodiment, the measuring arm 14 includes a housing 14a, which can be rectangular, and has an opening 14b. The first extension section 15 can be located on a longer side of the housing 14a. The first extension section 15 has a first indicator portion 16 which is used to show the rotational torque magnitude of the rod 1. For example, the first indicator portion 16 can have different color blocks, gradient colors, or a scale with marks and numbers. The present invention is not limited in this regard. In this embodiment, the first indicator portion 16 is a scale providing direct information for the user.

The rod 1 further includes a force applying arm 17. Preferably, an end of the force applying arm 17 is connected to the coupling portion 11 by integral formation. Preferably, the force applying arm 17 and the measuring arm 14 are disconnected from each other, and the force applying arm 17 and the measuring arm 14 are juxtaposed and connected to the coupling portion 11. The junction between the force applying arm 17 and the coupling portion 11 can serve as a fulcrum, such that the force applying arm 17 can elastically deform away from the measuring arm 14. In this embodiment, the minimum cross sectional area of the junction between the force applying arm 17 and the coupling portion 11 is smaller than 50% of the minimum cross sectional area of the coupling portion 11. Thus, the force applying arm 17 can easily deform about the fulcrum. The force applying arm 17 includes a second extension 18 extending in a direction the same as an extending direction of the first extension section 15. Namely, the second extension section 18 extends in the circumferential direction D. Preferably, the second extension section 18 is adjacent to the first extension section 15. Thus, when the force applying arm 17 moves away from the measuring arm 14, the second extension section 18 displaces relative to the first extension section 15. In this embodiment, the second extension section 18 extends into the housing 14a via the opening 14b.

The second extension section 18 has a second indicator portion 19 aligned with the first indicator portion 16. Thus, the second indicator portion 19 can show the rotational torque magnitude of the rod 1. Specifically, the second indicator portion 19 can include an indicator sign corresponding to the first indicator portion 16. For example, the second indicator portion 19 can be an arrow or a mark for pointing a colorful block, a gradient color, or a mark on the scale. In this embodiment, the second indicator portion 19 can be in the form of a triangular protrusion protruding from an edge of the second extension section 18. The opening 14b of the housing 14a can include a stop block 14c for stopping the second indicator portion 19. Thus, the first indicator portion 16 has a pre-set value at the stop block 14c, with the pre-set value being a threshold torque value. When the second indicator portion 19 abuts against the stop block 14c, the user can be reminded that the rotational torque of the rod 1 is too large, thereby reducing mistakes of the user during operation. Furthermore, the second indicator portion 19 can be colorful blocks, gradient colors, or a scale with marks and numbers, whereas the first indicator portion 16 can be a corresponding arrow or mark. The present invention is not limited in this regard.

With reference to FIGS. 1 and 2, the adaptor 2 includes an outer ring 2a and an inner ring 2b. The outer ring 2a is rotatable relative to the inner ring 2a in a single direction. An outer diameter of the outer ring 2a can be slightly larger than an inner diameter of the through-hole 12, such that the adaptor 2 can be coupled into the through-hole 12 by force fitting to increase the coupling stability between the adaptor 2 and through-hole 12. An outer periphery of the outer ring 2a can Dell have a plurality of first toothed structures 25, and an inner periphery of the through-hole 12 of the rod 1 does not match with the plurality of first toothed structures 25 to reduce the contact area between the outer periphery of the outer ring 2a and the inner periphery of the through-hole 12. This permits the adaptor 2 to be easily mounted into and easily removed out of the through-hole 12, increasing the use convenience. In this embodiment, each of two open ends 21 at upper and lower sides of the outer ring 2a has an inner annular ledge 22 to prevent disengagement of components in the outer ring 2a. An inner periphery of the outer ring 2a can include at least one unidirectional tooth 23 protruding outwards towards a central axis of the outer ring 2a.

Figure 4:
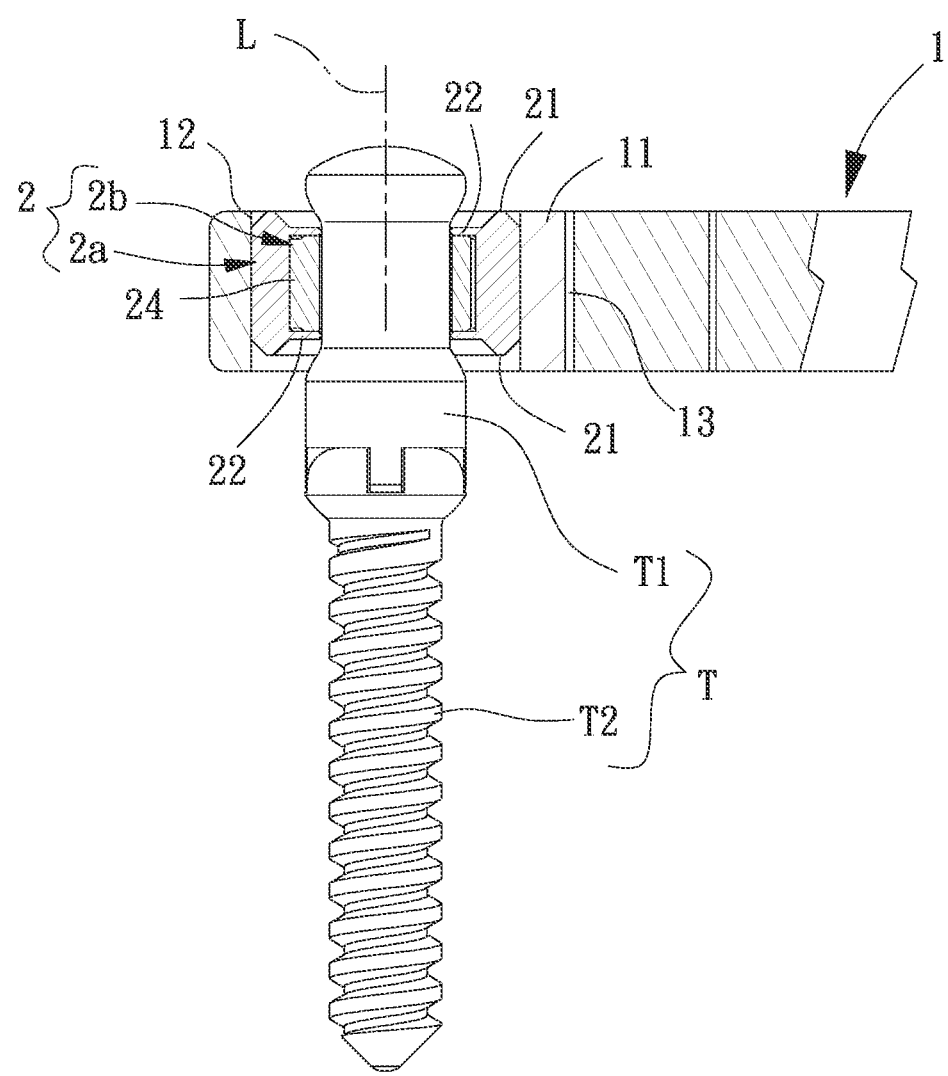
FIG. 4 is a partially sectioned view taken along section line 4-4 of the tool of FIG. 3.

With reference to FIGS. 3 and 4, the inner ring 2b can be disposed between the two inner annular ledges 22. The inner ring 2b can be a unidirectional wheel. Specifically, the outer periphery of the inner ring 2b includes a plurality of ratchet teeth 24, such that the outer ring 2a can only drive the inner ring 2b to rotate in the single direction. Namely, when the outer ring 2a is driven by an external force to rotate in a direction, the at least one unidirectional tooth 23 slides across each of the plurality of ratchet teeth 24. When the outer ring 2a rotates in a reverse direction, the at least one unidirectional tooth 23 will be stopped by the plurality of the ratchet teeth 24, such that the outer ring 2a can drive the inner ring 2b to rotate.

An inner diameter of the inner ring 2b can correspond to an outer diameter of a conventional bone nail unit T. Specifically, the conventional bone nail unit T includes a catching head T1 and a screw T2 detachably coupled to the catching head T1. The catching head T1 can be held by a user or actuated by a tool for operation, avoiding direct contact with the screw T2 to thereby avoid contamination to the screw T2. The inner diameter of the inner ring 2b can match with an outer diameter of the catching head T1. Thus, by simply changing an adaptor 2 of an associated inner diameter, the tool for a bone implant according to the present invention can be used with bone nail units T of various sizes. Preferably, the inner periphery of the inner ring 2b can include a plurality of second toothed structures 26 to permit the bone nail unit T to be easily placed into the inner ring 2b.

Figure 5:
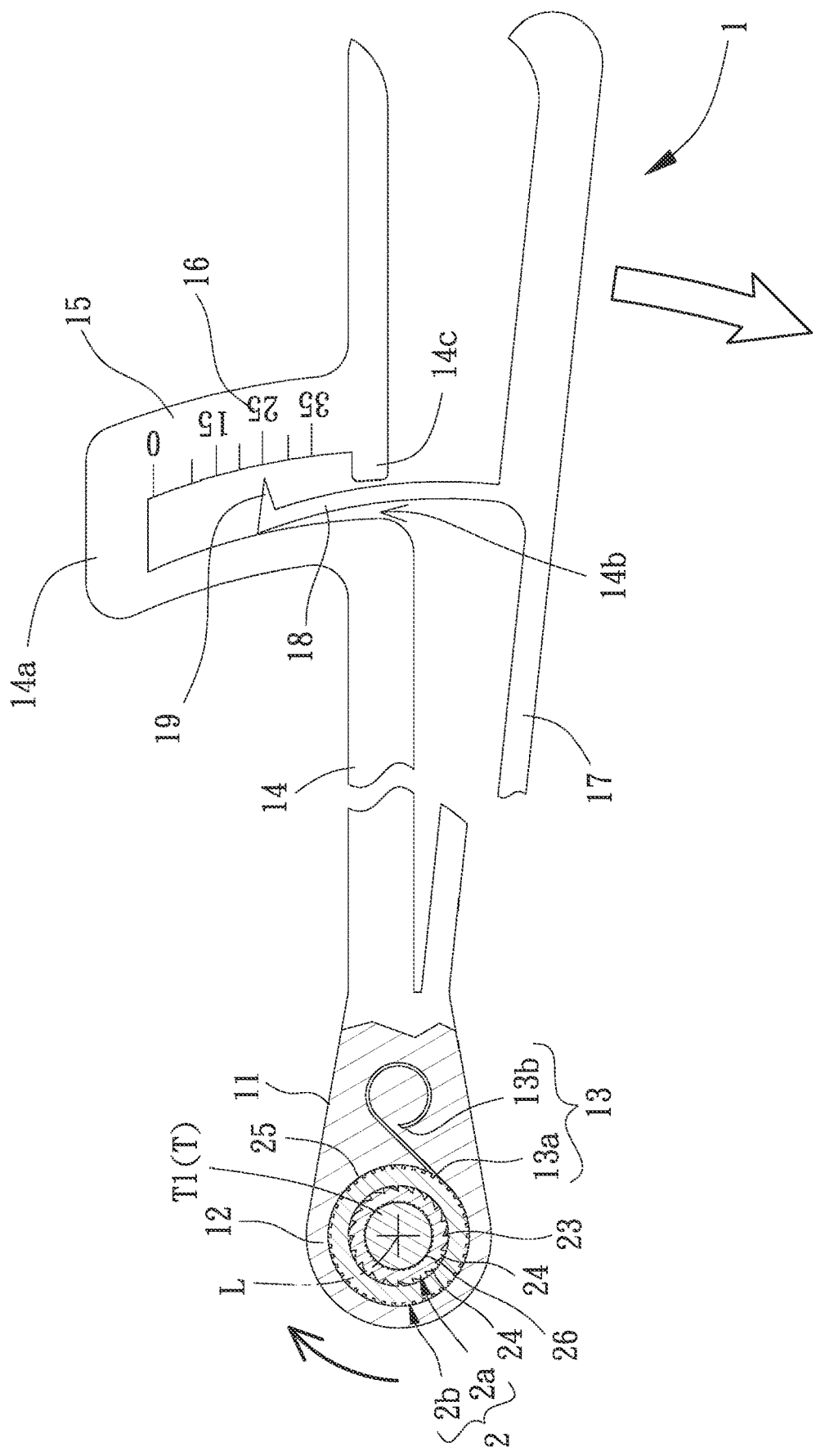
FIG. 5 is a diagrammatic view similar to FIG. 3, illustrating rotation of a rod of the tool of the embodiment according to the present invention.
Figure 6:
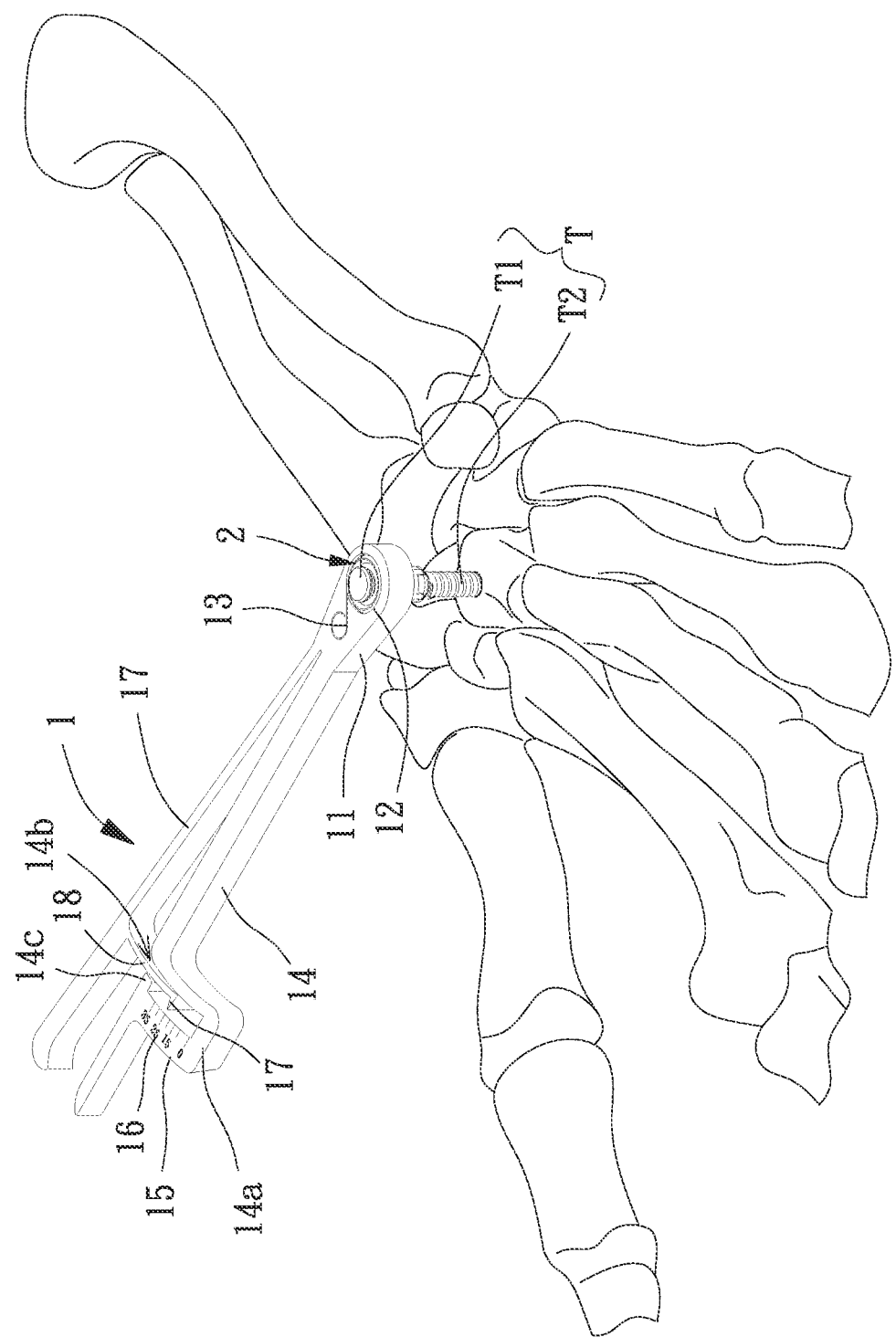
FIG. 6 is a diagrammatic view illustrating use of the tool of the embodiment according to the present invention for locking a bone nail unit into a bone tissue.

With reference to FIGS. 5 and 6, in use of the tool for a bone implant, the inner ring 2b of the adaptor 2 is coupled with the bone nail unit T. The user can rotate the force applying arm 17 in the clockwise direction to screw the bone nail unit T into the bone tissue of a pre-determined portion. By the torque created by applying a force to the force applying arm 17, the second extension section 18 of the force applying arm 17 displaces relative to the first extension section 15 of the measuring arm 14, and the first and second indicator portions 16 and 19 indicate the torque magnitude by the displacement magnitude of the second extension section 18. The first indicator portion 16 permits the elastic deformation extent of the force applying arm 17 to be converted into the distance between the corresponding hash markings based on the rigidity of the material of the rod 1, which elastic deformation extent is indicated by the first indicator portion 16 or the second indicator portion 19. Thus, the user can observe the displacement magnitude of the second extension section 18 relative to the first extension section 15 to rotate the force applying arm 17 and to control the torque to be within a proper range. Since the outer ring 2a can only drive the inner ring 2b to rotate in a single direction, the user can rotate the rod 1 in the clockwise direction and the counterclockwise direction in an alternating fashion to screw the bone nail unit T into the bone tissue. This permits the user to proceed with the operation within a limited space, increasing the use convenience.

Figure 7:
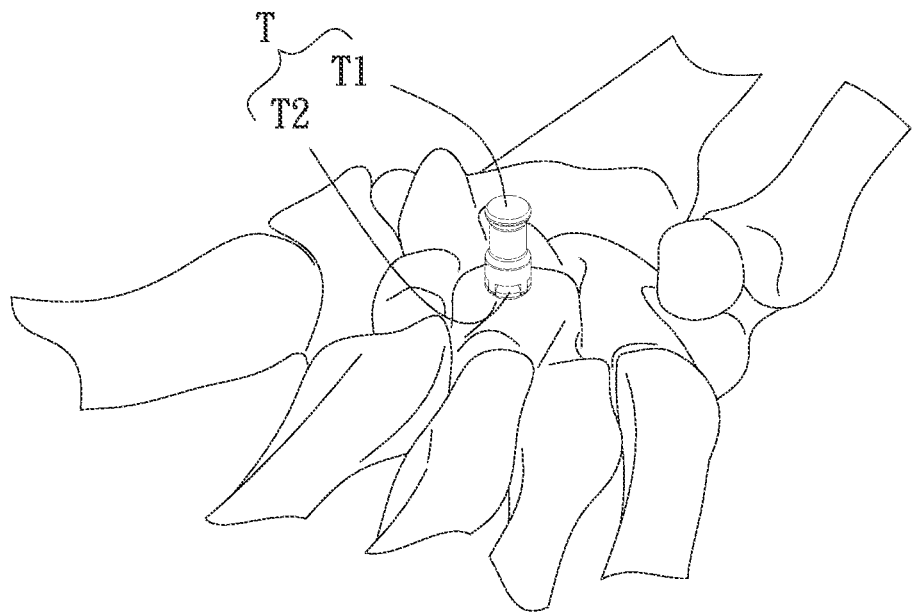
FIG. 7 is a diagrammatic view similar to FIG. 6 with the rod removed from the bone nail unit.

With reference to FIG. 7, when the screw T2 of the bone nail unit T is screwed into the bone tissue, the inner ring 2b can be detached from the catching head T1 of the bone nail unit T, and the catching head T1 is exposed outside of the bone tissue.

Figure 8:
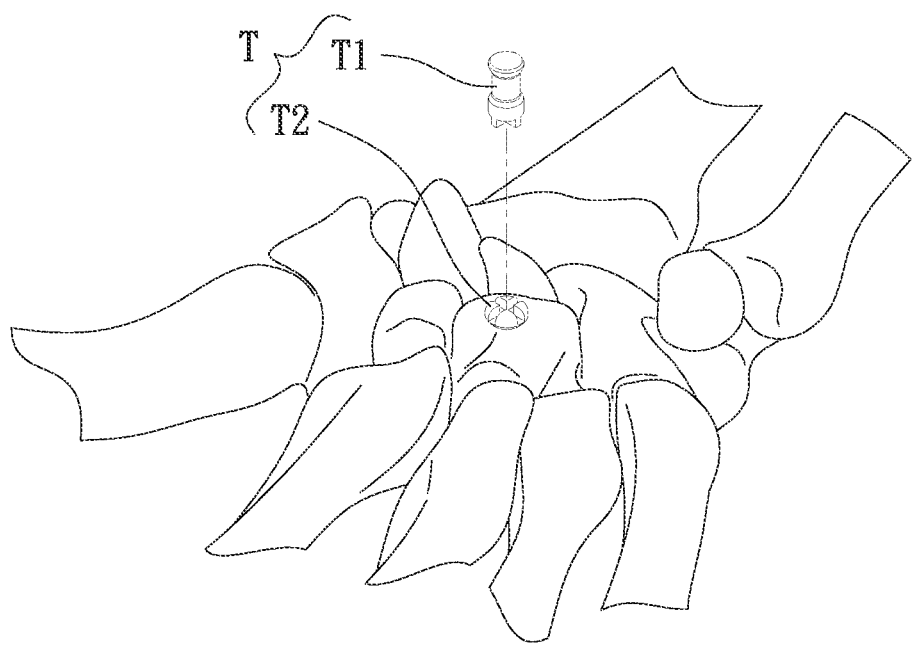
FIG. 8 is a diagrammatic view similar to FIG. 7 with a catching head removed from the bone nail unit.

With reference to FIG. 8, the user can then remove the catching head T1 to separate the catching head T1 from the screw T2, completing the bone nail implantation.

In view of the foregoing, according to the tool for a bone implant according to the present invention, the rod can be rotated by applying a force to the force applying arm. The torque created by the force applying arm can displace the second extension section relative to the first extension section, and the torque magnitude created by the force applying arm can be learned from the position of the second indicator portion relative to the first indicator portion. Thus, when the user screws the bone nail unit into a predetermined portion, the magnitude of the created torque can be known, and the torque can be controlled not to exceed 35 Ncm, avoiding injury to the bone tissue by an excessive torque while permitting the rod to be rotated by a most proper torque. Furthermore, the tool for a bone implant according to the present invention measures the torque magnitude with the elastic deformation of the force applying arm of the rod, and the rod can be disinfected and sterilized at high temperature, which is suitable for bone nail implantation, reducing the operation risks and improving the quality of the medical treatment.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A tool for a bone implant, comprising:
a rod including a coupling portion having a through-hole, wherein the rod further includes a measuring arm connected to the coupling portion and a force applying arm connected to the coupling portion, wherein the measuring arm includes a first extension section having a first indicator portion, wherein the force applying arm includes a second extension section having a second indicator portion, and wherein the force applying arm is elastically deformable away from the measuring arm to displace the second extension section relative to the first extension section; and
an adaptor including an outer ring and an inner ring, wherein each of two open ends at upper and lower sides of the outer ring has an annular ledge, wherein the inner ring is elastically deformable relative to the outer ring to permit the inner ring to be disposed between the annular ledges, wherein the outer ring is coupled in the through-hole of the rod, wherein the outer ring includes an outer periphery having a plurality of first toothed structures, wherein an inner periphery of the through-hole of the rod does not match with the plurality of first toothed structures to reduce a contact area between the outer periphery of the outer ring and the inner periphery of the through-hole, wherein the inner ring includes an inner periphery having a plurality of second toothed structures, and wherein the outer ring is rotatable relative to the inner ring in a single direction.

2. The tool for the bone implant as claimed in claim 1, wherein the rod is made of a titanium alloy.

3. The tool for the bone implant as claimed in claim 2, wherein the titanium alloy is $Ti_6Al_4V$.

4. The tool for the bone implant as claimed in claim 1, wherein the coupling portion includes an expansion gap having an open end intercommunicating with the through-hole, and wherein the expansion gap extends in the coupling portion to form a closed end.

5. The tool for the bone implant as claimed in claim 1, wherein the expansion gap extends in the coupling portion along a circular path.

6. The tool for the bone implant as claimed in claim 1, wherein the measuring arm and the force applying arm are disconnected from each other and are connected to the coupling portion in parallel.

7. The tool for the bone implant as claimed in claim 1, wherein the measuring arm includes a housing having an opening, and wherein the second extension extends into the housing via the opening.

8. The tool for the bone implant as claimed in claim 1, wherein the tool has a first width at a junction between the force applying arm and the coupling portion, and wherein the first width is smaller than a maximum second width of the coupling portion.

9. The tool for the bone implant as claimed in claim 1, wherein the outer ring includes an inner periphery having at least one unidirectional tooth, wherein the inner ring includes an outer periphery having a plurality of ratchet teeth, and wherein the outer ring is capable of driving the inner ring to rotate in the single direction only.

* * * * *